United States Patent
Begnaud et al.

(10) Patent No.: US 7,869,885 B2
(45) Date of Patent: Jan. 11, 2011

(54) THRESHOLD OPTIMIZATION FOR TISSUE STIMULATION THERAPY

(75) Inventors: Jason D. Begnaud, Houston, TX (US); Chris G. Dupont, League City, TX (US); Jerry J. Kolafa, Richmond, TX (US); Huan D. Nguyen, Houston, TX (US)

(73) Assignee: Cyberonics, Inc, Houston, TX (US)

( * ) Notice: Subject to any disclaimer, the term of this patent is extended or adjusted under 35 U.S.C. 154(b) by 1096 days.

(21) Appl. No.: 11/414,393

(22) Filed: Apr. 28, 2006

(65) Prior Publication Data

US 2007/0255351 A1 Nov. 1, 2007

(51) Int. Cl.
*A61N 1/36* (2006.01)

(52) U.S. Cl. .......................... 607/118; 607/46
(58) Field of Classification Search .................. 607/45, 607/46, 118
See application file for complete search history.

(56) References Cited

U.S. PATENT DOCUMENTS

| | | |
|---|---|---|
| 3,760,812 A | 9/1973 | Timm et al. |
| 3,796,221 A | 3/1974 | Hagfors |
| 4,107,469 A | 8/1978 | Jenkins |
| 4,305,402 A | 12/1981 | Katims |
| 4,338,945 A | 7/1982 | Kosugi et al. |
| 4,424,812 A | 1/1984 | Lesnick |
| 4,431,000 A | 2/1984 | Butler et al. |
| 4,459,989 A | 7/1984 | Borkan |
| 4,503,863 A | 3/1985 | Katims |
| 4,541,432 A | 9/1985 | Molina-Negro et al. |
| 4,573,481 A | 3/1986 | Bullara |
| 4,577,316 A | 3/1986 | Schiff |
| 4,590,946 A | 5/1986 | Loeb |
| 4,592,339 A | 6/1986 | Kuzmak et al. |
| 4,606,349 A | 8/1986 | Livingston et al. |
| 4,608,985 A | 9/1986 | Crish et al. |
| 4,612,934 A | 9/1986 | Borkan |
| 4,625,308 A | 11/1986 | Kim et al. |
| 4,628,942 A | 12/1986 | Sweeney et al. |
| 4,649,936 A | 3/1987 | Ungar et al. |
| 4,702,254 A | 10/1987 | Zarbara |

(Continued)

FOREIGN PATENT DOCUMENTS

CA 2339971 6/2004

(Continued)

OTHER PUBLICATIONS

Bachman, D.,S. et al.; "Effects Of Vagal Volleys And Serotonin On Units Of Cingulate Cortex in Monkeys;" Brain Research, vol. 130 (1977). pp. 253-269.

(Continued)

*Primary Examiner*—Carl H Layno
*Assistant Examiner*—Brian T Gedeon
(74) *Attorney, Agent, or Firm*—Conley Rose, P.C.; Timothy L. Scott; Darrell N. Fuller

(57) ABSTRACT

Methods and systems for determining an optimal therapeutic window of parameter settings for nerve stimulation therapy are described herein. The disclosed techniques generally utilize one or more parameter sweeps to determine upper and lower threshold settings. The determination of the optimal therapeutic window may be performed during or after implantation.

18 Claims, 4 Drawing Sheets

U.S. PATENT DOCUMENTS

| | | |
|---|---|---|
| 4,793,353 A | 12/1988 | Borkan |
| 4,867,164 A | 9/1989 | Zabara |
| 4,920,979 A | 5/1990 | Bullara |
| 4,949,721 A | 8/1990 | Toriu et al. |
| 4,977,895 A | 12/1990 | Tannenbaum |
| 5,025,807 A | 6/1991 | Zarbara |
| 5,081,987 A | 1/1992 | Nigam |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,205,285 A | 4/1993 | Baker, Jr. |
| 5,215,086 A | 6/1993 | Terry, Jr. et al. |
| 5,222,494 A | 6/1993 | Baker, Jr. |
| 5,231,988 A | 8/1993 | Wernicke et al. |
| 5,235,980 A | 8/1993 | Varrichio et al. |
| 5,263,480 A | 11/1993 | Wernicke et al. |
| 5,269,303 A | 12/1993 | Wernicke et al. |
| 5,299,569 A | 4/1994 | Wernicke et al. |
| 5,330,507 A | 7/1994 | Schwartz |
| 5,330,515 A | 7/1994 | Rutecki et al. |
| 5,334,221 A | 8/1994 | Bardy |
| 5,354,320 A | 10/1994 | Schaldach et al. |
| 5,411,531 A | 5/1995 | Hill et al. |
| 5,411,540 A | 5/1995 | Edell et al. |
| 5,423,872 A | 6/1995 | Cigaina |
| 5,507,784 A | 4/1996 | Hill et al. |
| 5,522,862 A | 6/1996 | Testerman et al. |
| 5,522,865 A | 6/1996 | Schulman et al. |
| 5,540,730 A | 7/1996 | Terry, Jr. et al. |
| 5,540,734 A | 7/1996 | Zabara |
| 5,571,150 A | 11/1996 | Wernicke et al. |
| 5,601,617 A | 2/1997 | Loeb et al. |
| 5,611,350 A | 3/1997 | John |
| 5,645,570 A | 7/1997 | Corbucci |
| 5,651,378 A | 7/1997 | Matheny et al. |
| 5,658,318 A | 8/1997 | Stroetmann et al. |
| 5,690,681 A | 11/1997 | Geddes et al. |
| 5,690,688 A | 11/1997 | Noren et al. |
| 5,690,691 A | 11/1997 | Chen et al. |
| 5,700,282 A | 12/1997 | Zabara |
| 5,702,428 A | 12/1997 | Tippey et al. |
| 5,702,429 A | 12/1997 | King |
| 5,707,400 A | 1/1998 | Terry, Jr. et al. |
| 5,755,750 A | 5/1998 | Petruska et al. |
| 5,792,212 A | 8/1998 | Weijand |
| 5,800,474 A | 9/1998 | Benabid et al. |
| 5,814,092 A | 9/1998 | King |
| 5,836,994 A | 11/1998 | Bourgeois |
| 5,861,014 A | 1/1999 | Familoni |
| 5,913,882 A | 6/1999 | King |
| 5,916,239 A | 6/1999 | Geddes et al. |
| 5,928,272 A | 7/1999 | Adkins et al. |
| 5,941,906 A | 8/1999 | Barreras, Sr. et al. |
| 5,995,868 A | 11/1999 | Dorfmeister et al. |
| 6,002,966 A | 12/1999 | Loeb et al. |
| 6,016,449 A | 1/2000 | Fischell et al. |
| 6,041,258 A | 3/2000 | Cigaina et al. |
| 6,083,249 A | 7/2000 | Familoni |
| 6,101,412 A | 8/2000 | Duhaylongsod |
| 6,104,955 A | 8/2000 | Bourgeois |
| 6,104,956 A | 8/2000 | Naritoku et al. |
| 6,115,628 A | 9/2000 | Stadler et al. |
| 6,132,361 A | 10/2000 | Epstein et al. |
| 6,141,590 A | 10/2000 | Renirie et al. |
| 6,161,044 A | 12/2000 | Silverstone |
| 6,167,311 A | 12/2000 | Rezai |
| 6,175,764 B1 | 1/2001 | Loeb et al. |
| 6,188,929 B1 | 2/2001 | Giordano |
| 6,219,580 B1 | 4/2001 | Faltys et al. |
| 6,221,908 B1 | 4/2001 | Kilgard et al. |
| 6,238,423 B1 | 5/2001 | Bardy |
| 6,249,704 B1 | 6/2001 | Maltan et al. |
| 6,253,109 B1 | 6/2001 | Gielen |
| 6,266,564 B1 | 7/2001 | Hill et al. |
| 6,269,270 B1 | 7/2001 | Boveja |
| 6,295,472 B1 | 9/2001 | Rubinstein et al. |
| 6,304,775 B1 | 10/2001 | Iasemidis et al. |
| 6,308,102 B1 | 10/2001 | Sieracki |
| 6,324,421 B1 | 11/2001 | Stadler et al. |
| 6,327,503 B1 | 12/2001 | Familoni |
| 6,339,725 B1 | 1/2002 | Naritoku et al. |
| 6,341,236 B1 | 1/2002 | Osorio et al. |
| 6,353,762 B1 | 3/2002 | Baudino et al. |
| 6,356,788 B2 | 3/2002 | Boveja |
| 6,358,203 B2 | 3/2002 | Bardy |
| 6,366,813 B1 | 4/2002 | DiLorenzo |
| 6,366,814 B1 | 4/2002 | Boveja |
| 6,374,140 B1 | 4/2002 | Rise |
| 6,381,493 B1 | 4/2002 | Stadler et al. |
| 6,381,496 B1 | 4/2002 | Meadows et al. |
| 6,381,499 B1 | 4/2002 | Taylor et al. |
| 6,418,344 B1 | 7/2002 | Rezai et al. |
| 6,425,852 B1 | 7/2002 | Epstein et al. |
| 6,438,423 B1 | 8/2002 | Rezai et al. |
| 6,449,512 B1 | 9/2002 | Boveja |
| 6,453,199 B1 | 9/2002 | Kobozev |
| 6,459,936 B2 | 10/2002 | Fischell et al. |
| 6,463,328 B1 | 10/2002 | John |
| 6,466,822 B1 | 10/2002 | Pless |
| 6,473,639 B1 | 10/2002 | Fischell et al. |
| 6,473,644 B1 | 10/2002 | Terry, Jr. et al. |
| 6,477,417 B1 | 11/2002 | Levine |
| 6,477,418 B2 | 11/2002 | Plicchi et al. |
| 6,480,743 B1 | 11/2002 | Kirkpatrick et al. |
| 6,484,132 B1 | 11/2002 | Hively et al. |
| 6,487,446 B1 | 11/2002 | Hill et al. |
| 6,505,074 B2 | 1/2003 | Boveja et al. |
| 6,522,928 B2 | 2/2003 | Whitehurst et al. |
| 6,532,388 B1 | 3/2003 | Hill et al. |
| 6,549,804 B1 | 4/2003 | Osorio et al. |
| 6,556,868 B2 | 4/2003 | Naritoku et al. |
| 6,564,102 B1 | 5/2003 | Boveja |
| 6,565,503 B2 | 5/2003 | Leysieffer et al. |
| 6,579,280 B1 | 6/2003 | Kovach et al. |
| 6,587,719 B1 | 7/2003 | Barrett et al. |
| 6,587,724 B2 | 7/2003 | Mann |
| 6,587,726 B2 | 7/2003 | Lurie et al. |
| 6,587,727 B2 | 7/2003 | Osorio et al. |
| 6,591,138 B1 | 7/2003 | Fischell et al. |
| 6,594,524 B2 | 7/2003 | Esteller et al. |
| 6,600,953 B2 | 7/2003 | Flesler et al. |
| 6,609,025 B2 | 8/2003 | Barrett et al. |
| 6,609,030 B1 | 8/2003 | Rezai et al. |
| 6,609,031 B1 | 8/2003 | Law et al. |
| 6,610,713 B2 | 8/2003 | Tracey |
| 6,611,715 B1 | 8/2003 | Boveja |
| 6,612,983 B1 | 9/2003 | Marchal |
| 6,615,081 B1 | 9/2003 | Boveja |
| 6,615,084 B1 | 9/2003 | Cigaina |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,656,960 B2 | 12/2003 | Puskas |
| 6,662,053 B2 | 12/2003 | Borkan |
| 6,668,191 B1 | 12/2003 | Boveja |
| 6,671,547 B2 | 12/2003 | Lyster et al. |
| 6,671,555 B2 | 12/2003 | Gielen et al. |
| 6,671,556 B2 | 12/2003 | Osorio et al. |
| 6,684,104 B2 | 1/2004 | Gordon et al. |
| 6,684,105 B2 | 1/2004 | Cohen et al. |
| 6,690,973 B2 | 2/2004 | Hill et al. |

| | | |
|---|---|---|
| 6,690,974 B2 | 2/2004 | Archer et al. |
| 6,708,064 B2 | 3/2004 | Rezai |
| 6,721,603 B2 | 4/2004 | Zabara et al. |
| 6,731,979 B2 | 5/2004 | MacDonald |
| 6,731,986 B2 | 5/2004 | Mann |
| 6,754,536 B2 | 6/2004 | Swoyer et al. |
| 6,760,626 B1 | 7/2004 | Boveja |
| 6,764,498 B2 | 7/2004 | Mische |
| 6,768,969 B1 | 7/2004 | Nikitin et al. |
| 6,775,573 B2 | 8/2004 | Schuler et al. |
| 6,793,670 B2 | 9/2004 | Osorio et al. |
| 6,819,956 B2 | 11/2004 | DiLorenzo |
| 6,826,428 B1 | 11/2004 | Chen et al. |
| 6,832,114 B1 | 12/2004 | Whitehurst et al. |
| 6,853,862 B1 | 2/2005 | Marchal et al. |
| 6,885,888 B2 | 4/2005 | Rezai |
| 6,895,278 B1 | 5/2005 | Gordon |
| 6,904,390 B2 | 6/2005 | Nikitin et al. |
| 6,907,295 B2 | 6/2005 | Gross et al. |
| 6,920,357 B2 | 7/2005 | Osorio et al. |
| 6,934,580 B1 | 8/2005 | Osorio et al. |
| 6,944,501 B1 | 9/2005 | Pless |
| 6,961,618 B2 | 11/2005 | Osorio et al. |
| 7,006,859 B1 | 2/2006 | Osorio et al. |
| 7,006,872 B2 | 2/2006 | Gielen et al. |
| 7,050,856 B2 | 5/2006 | Stypulkowski |
| 7,054,686 B2 | 5/2006 | MacDonald |
| 7,146,217 B2 | 12/2006 | Firlik et al. |
| 7,167,750 B2 | 1/2007 | Knudson et al. |
| 7,177,678 B1 | 2/2007 | Osorio et al. |
| 7,188,053 B2 | 3/2007 | Nikitin et al. |
| 7,204,833 B1 | 4/2007 | Osorio et al. |
| 7,209,787 B2 | 4/2007 | DiLorenzo |
| 7,231,254 B2 | 6/2007 | DiLorenzo |
| 7,236,830 B2 | 6/2007 | Gliner |
| 7,236,831 B2 | 6/2007 | Firlik et al. |
| 7,242,983 B2 | 7/2007 | Frei et al. |
| 7,242,984 B2 | 7/2007 | DiLorenzo |
| 7,340,302 B1 | 3/2008 | Falkenberg et al. |
| 2001/0034541 A1 | 10/2001 | Lyden |
| 2001/0037220 A1 | 11/2001 | Merry et al. |
| 2002/0052539 A1 | 5/2002 | Haller et al. |
| 2002/0065509 A1 | 5/2002 | Lebel et al. |
| 2002/0072782 A1 | 6/2002 | Osorio et al. |
| 2002/0082480 A1 | 6/2002 | Riff et al. |
| 2002/0099412 A1 | 7/2002 | Fischell et al. |
| 2002/0099417 A1 | 7/2002 | Naritoku et al. |
| 2002/0116030 A1 | 8/2002 | Rezai |
| 2002/0120310 A1 | 8/2002 | Linden et al. |
| 2002/0133204 A1 | 9/2002 | Hrdlicka |
| 2002/0143368 A1 | 10/2002 | Bakels et al. |
| 2002/0151939 A1 | 10/2002 | Rezai |
| 2002/0153901 A1 | 10/2002 | Davis et al. |
| 2002/0188214 A1 | 12/2002 | Misczynski et al. |
| 2003/0028226 A1 | 2/2003 | Thompson et al. |
| 2003/0055457 A1 | 3/2003 | MacDonald |
| 2003/0074032 A1 | 4/2003 | Gliner |
| 2003/0083716 A1 | 5/2003 | Nicolelis et al. |
| 2003/0088274 A1 | 5/2003 | Gliner et al. |
| 2003/0095648 A1 | 5/2003 | Kaib et al. |
| 2003/0097161 A1 | 5/2003 | Firlik et al. |
| 2003/0109903 A1 | 6/2003 | Berrang et al. |
| 2003/0125786 A1 | 7/2003 | Gliner et al. |
| 2003/0130706 A1 | 7/2003 | Sheffield et al. |
| 2003/0135248 A1* | 7/2003 | Stypulkowski ............... 607/73 |
| 2003/0144711 A1 | 7/2003 | Pless et al. |
| 2003/0144829 A1 | 7/2003 | Geatz et al. |
| 2003/0181954 A1 | 9/2003 | Rezai |
| 2003/0181958 A1 | 9/2003 | Dobak |
| 2003/0181959 A1 | 9/2003 | Dobak |
| 2003/0208212 A1 | 11/2003 | Cigaina |
| 2003/0210147 A1 | 11/2003 | Humbard |
| 2003/0212440 A1 | 11/2003 | Boveja |
| 2003/0236558 A1 | 12/2003 | Whitehurst et al. |
| 2004/0006278 A1 | 1/2004 | Webb et al. |
| 2004/0015205 A1 | 1/2004 | Whitehurst et al. |
| 2004/0036377 A1 | 2/2004 | Mezinis |
| 2004/0039424 A1 | 2/2004 | Merritt et al. |
| 2004/0088024 A1 | 5/2004 | Firlik et al. |
| 2004/0111139 A1 | 6/2004 | McCreery |
| 2004/0112894 A1 | 6/2004 | Varma |
| 2004/0122484 A1 | 6/2004 | Hatlestad et al. |
| 2004/0122485 A1 | 6/2004 | Stahmann et al. |
| 2004/0122489 A1 | 6/2004 | Mazar et al. |
| 2004/0133119 A1 | 7/2004 | Osorio et al. |
| 2004/0138516 A1 | 7/2004 | Osorio et al. |
| 2004/0138517 A1 | 7/2004 | Osorio et al. |
| 2004/0138518 A1 | 7/2004 | Rise et al. |
| 2004/0138647 A1 | 7/2004 | Osorio et al. |
| 2004/0138711 A1 | 7/2004 | Osorio et al. |
| 2004/0147969 A1 | 7/2004 | Mann et al. |
| 2004/0147992 A1 | 7/2004 | Bluger et al. |
| 2004/0153129 A1 | 8/2004 | Pless et al. |
| 2004/0158119 A1 | 8/2004 | Osorio et al. |
| 2004/0158165 A1 | 8/2004 | Yonce et al. |
| 2004/0167583 A1 | 8/2004 | Knudson et al. |
| 2004/0167587 A1 | 8/2004 | Thompson |
| 2004/0172085 A1 | 9/2004 | Knudson et al. |
| 2004/0172088 A1 | 9/2004 | Knudson et al. |
| 2004/0172089 A1 | 9/2004 | Whitehurst et al. |
| 2004/0172091 A1 | 9/2004 | Rezai |
| 2004/0172094 A1 | 9/2004 | Cohen et al. |
| 2004/0176812 A1 | 9/2004 | Knudson et al. |
| 2004/0176831 A1 | 9/2004 | Gliner et al. |
| 2004/0193231 A1 | 9/2004 | David et al. |
| 2004/0199146 A1 | 10/2004 | Rogers et al. |
| 2004/0199187 A1 | 10/2004 | Loughran |
| 2004/0199212 A1 | 10/2004 | Fischell et al. |
| 2004/0210270 A1 | 10/2004 | Erickson |
| 2004/0210274 A1 | 10/2004 | Bauhahn et al. |
| 2004/0249302 A1 | 12/2004 | Donoghue et al. |
| 2004/0249416 A1 | 12/2004 | Yun et al. |
| 2004/0260346 A1 | 12/2004 | Overall et al. |
| 2004/0263172 A1 | 12/2004 | Gray et al. |
| 2005/0004615 A1 | 1/2005 | Sanders |
| 2005/0004621 A1 | 1/2005 | Boveja et al. |
| 2005/0010262 A1 | 1/2005 | Rezai et al. |
| 2005/0015128 A1 | 1/2005 | Rezai et al. |
| 2005/0016657 A1 | 1/2005 | Bluger |
| 2005/0020887 A1 | 1/2005 | Goldberg |
| 2005/0021092 A1 | 1/2005 | Yun et al. |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0027284 A1 | 2/2005 | Lozano et al. |
| 2005/0028026 A1 | 2/2005 | Shirley et al. |
| 2005/0033378 A1 | 2/2005 | Sheffield et al. |
| 2005/0033379 A1 | 2/2005 | Lozano et al. |
| 2005/0038326 A1 | 2/2005 | Mathur |
| 2005/0038484 A1 | 2/2005 | Knudson et al. |
| 2005/0049515 A1 | 3/2005 | Misczynski et al. |
| 2005/0049655 A1 | 3/2005 | Boveja et al. |
| 2005/0060007 A1 | 3/2005 | Goetz |
| 2005/0060008 A1 | 3/2005 | Goetz |
| 2005/0060009 A1 | 3/2005 | Goetz |
| 2005/0060010 A1 | 3/2005 | Goetz |
| 2005/0065562 A1 | 3/2005 | Rezai |
| 2005/0065573 A1 | 3/2005 | Rezai |
| 2005/0065574 A1 | 3/2005 | Rezai |
| 2005/0065575 A1 | 3/2005 | Dobak |
| 2005/0070971 A1 | 3/2005 | Fowler et al. |
| 2005/0075679 A1 | 4/2005 | Gliner et al. |
| 2005/0075680 A1 | 4/2005 | Lowry et al. |

| | | |
|---|---|---|
| 2005/0075681 A1 | 4/2005 | Rezai et al. |
| 2005/0075691 A1 | 4/2005 | Phillips et al. |
| 2005/0075701 A1 | 4/2005 | Shafer |
| 2005/0075702 A1 | 4/2005 | Shafer |
| 2005/0088145 A1 | 4/2005 | Loch |
| 2005/0101873 A1 | 5/2005 | Misczynski et al. |
| 2005/0102002 A1 | 5/2005 | Salo et al. |
| 2005/0107753 A1 | 5/2005 | Rezai et al. |
| 2005/0107842 A1 | 5/2005 | Rezai |
| 2005/0107858 A1 | 5/2005 | Bulger |
| 2005/0113705 A1 | 5/2005 | Fischell et al. |
| 2005/0113744 A1 | 5/2005 | Donoghue et al. |
| 2005/0119703 A1 | 6/2005 | DiLorenzo |
| 2005/0124901 A1 | 6/2005 | Misczynski et al. |
| 2005/0131467 A1 | 6/2005 | Boveja et al. |
| 2005/0131485 A1 | 6/2005 | Knudson et al. |
| 2005/0131486 A1 | 6/2005 | Boveja et al. |
| 2005/0131493 A1 | 6/2005 | Boveja et al. |
| 2005/0131506 A1 | 6/2005 | Rezai et al. |
| 2005/0137480 A1 | 6/2005 | Alt et al. |
| 2005/0143781 A1 | 6/2005 | Carbunaru et al. |
| 2005/0143786 A1 | 6/2005 | Boveja et al. |
| 2005/0148893 A1 | 7/2005 | Misczynski et al. |
| 2005/0148894 A1 | 7/2005 | Misczynski et al. |
| 2005/0148895 A1 | 7/2005 | Misczynski et al. |
| 2005/0153885 A1 | 7/2005 | Yun et al. |
| 2005/0154425 A1 | 7/2005 | Boveja et al. |
| 2005/0154435 A1 | 7/2005 | Stern et al. |
| 2005/0159789 A1 | 7/2005 | Brockway et al. |
| 2005/0161052 A1 | 7/2005 | Rezai et al. |
| 2005/0165458 A1 | 7/2005 | Boveja et al. |
| 2005/0177192 A1 | 8/2005 | Rezai et al. |
| 2005/0177200 A1 | 8/2005 | George et al. |
| 2005/0177206 A1 | 8/2005 | North et al. |
| 2005/0182389 A1 | 8/2005 | LaPorte et al. |
| 2005/0187590 A1 | 8/2005 | Boveja et al. |
| 2005/0187593 A1 | 8/2005 | Housworth et al. |
| 2005/0187796 A1 | 8/2005 | Rosenfeld et al. |
| 2005/0192644 A1 | 9/2005 | Boveja et al. |
| 2005/0197590 A1 | 9/2005 | Osorio et al. |
| 2005/0222631 A1 | 10/2005 | Dalal et al. |
| 2005/0228693 A1 | 10/2005 | Webb et al. |
| 2005/0240246 A1 | 10/2005 | Lee et al. |
| 2005/0245944 A1 | 11/2005 | Rezai |
| 2005/0245971 A1 | 11/2005 | Brockway et al. |
| 2005/0245990 A1 | 11/2005 | Roberson |
| 2005/0261542 A1 | 11/2005 | Riehl |
| 2005/0267550 A1 | 12/2005 | Hess et al. |
| 2005/0272280 A1 | 12/2005 | Osypka |
| 2005/0277872 A1 | 12/2005 | Colby et al. |
| 2005/0277998 A1 | 12/2005 | Tracey et al. |
| 2005/0283200 A1 | 12/2005 | Rezai et al. |
| 2005/0283201 A1 | 12/2005 | Machado et al. |
| 2005/0283208 A1 | 12/2005 | Von Arx et al. |
| 2005/0288600 A1 | 12/2005 | Zhang et al. |
| 2005/0288736 A1 | 12/2005 | Persen et al. |
| 2005/0288760 A1 | 12/2005 | Machado et al. |
| 2006/0009815 A1 | 1/2006 | Boveja |
| 2006/0020292 A1 | 1/2006 | Goetz et al. |
| 2006/0020491 A1 | 1/2006 | Mongeon et al. |
| 2006/0041222 A1 | 2/2006 | Dewing et al. |
| 2006/0041223 A1 | 2/2006 | Dewing et al. |
| 2006/0041287 A1 | 2/2006 | Dewing et al. |
| 2006/0047205 A1 | 3/2006 | Ludomirsky et al. |
| 2006/0052843 A1 | 3/2006 | Elsner et al. |
| 2006/0058597 A1 | 3/2006 | Machado et al. |
| 2006/0064133 A1 | 3/2006 | Von Arx et al. |
| 2006/0064134 A1 | 3/2006 | Mazar et al. |
| 2006/0064143 A1 | 3/2006 | Von Arx et al. |
| 2006/0069322 A1 | 3/2006 | Zhang et al. |
| 2006/0074450 A1 | 4/2006 | Boveja |
| 2006/0079936 A1 | 4/2006 | Boveja |
| 2006/0079942 A1 | 4/2006 | Deno et al. |
| 2006/0079945 A1 | 4/2006 | Libbus |
| 2006/0085046 A1 | 4/2006 | Rezai et al. |
| 2006/0094971 A1 | 5/2006 | Drew |
| 2006/0095081 A1 | 5/2006 | Zhou et al. |
| 2006/0100667 A1 | 5/2006 | Machado et al. |
| 2006/0106430 A1 | 5/2006 | Fowler et al. |
| 2006/0106431 A1 | 5/2006 | Wyler et al. |
| 2006/0111644 A1 | 5/2006 | Guttag et al. |
| 2006/0122525 A1 | 6/2006 | Shusterman |
| 2006/0122667 A1 | 6/2006 | Chavan et al. |
| 2006/0122864 A1 | 6/2006 | Gottesman et al. |
| 2006/0135877 A1 | 6/2006 | Giftakis et al. |
| 2006/0135881 A1 | 6/2006 | Giftakis et al. |
| 2006/0155495 A1 | 7/2006 | Osorio et al. |
| 2006/0161459 A9 | 7/2006 | Rosenfeld et al. |
| 2006/0167497 A1 | 7/2006 | Armstrong et al. |
| 2006/0173493 A1 | 8/2006 | Armstrong et al. |
| 2006/0173522 A1 | 8/2006 | Osorio |
| 2006/0190056 A1 | 8/2006 | Fowler et al. |
| 2006/0195155 A1 | 8/2006 | Firlik et al. |
| 2006/0195163 A1 | 8/2006 | KenKnight et al. |
| 2006/0200206 A1 | 9/2006 | Firlik et al. |
| 2006/0212091 A1 | 9/2006 | Lozano et al. |
| 2006/0217780 A1 | 9/2006 | Gliner et al. |
| 2006/0220839 A1 | 10/2006 | Fifolt et al. |
| 2006/0224067 A1 | 10/2006 | Giftakis et al. |
| 2006/0224191 A1 | 10/2006 | DiLorenzo |
| 2006/0241697 A1 | 10/2006 | Libbus et al. |
| 2006/0241725 A1 | 10/2006 | Libbus et al. |
| 2006/0253164 A1 | 11/2006 | Zhang et al. |
| 2006/0253168 A1 | 11/2006 | Wyler et al. |
| 2006/0253169 A1 | 11/2006 | Wyler et al. |
| 2006/0253170 A1 | 11/2006 | Wyler et al. |
| 2006/0253171 A1 | 11/2006 | Wyler et al. |
| 2006/0259095 A1 | 11/2006 | Wyler et al. |
| 2006/0264730 A1 | 11/2006 | Stivoric et al. |
| 2006/0265018 A1 | 11/2006 | Smith et al. |
| 2006/0271409 A1 | 11/2006 | Rosenfeld et al. |
| 2006/0293720 A1 | 12/2006 | DiLorenzo |
| 2007/0027486 A1 | 2/2007 | Armstrong et al. |
| 2007/0032734 A1 | 2/2007 | Najafi et al. |
| 2007/0032834 A1 | 2/2007 | Gliner et al. |
| 2007/0038262 A1 | 2/2007 | Kieval et al. |
| 2007/0043392 A1 | 2/2007 | Gliner et al. |
| 2007/0043400 A1* | 2/2007 | Donders et al. ............... 607/45 |
| 2007/0055320 A1 | 3/2007 | Weinand et al. |
| 2007/0073150 A1 | 3/2007 | Gopalsami et al. |
| 2007/0073346 A1 | 3/2007 | Corbucci et al. |
| 2007/0073355 A1 | 3/2007 | DiLorenzo |
| 2007/0078491 A1 | 4/2007 | Siejko et al. |
| 2007/0088403 A1 | 4/2007 | Wyler et al. |
| 2007/0088404 A1 | 4/2007 | Wyler et al. |
| 2007/0088405 A1 | 4/2007 | Jacobson et al. |
| 2007/0100278 A1 | 5/2007 | Frei et al. |
| 2007/0100397 A1 | 5/2007 | Seeberger et al. |
| 2007/0100398 A1 | 5/2007 | Sloan |
| 2007/0112393 A1 | 5/2007 | Gliner et al. |
| 2007/0123946 A1 | 5/2007 | Masoud |
| 2007/0135855 A1 | 6/2007 | Foshee et al. |
| 2007/0142862 A1 | 6/2007 | DiLorenzo |
| 2007/0142873 A1 | 6/2007 | Esteller et al. |
| 2007/0149952 A1 | 6/2007 | Bland et al. |
| 2007/0150011 A1 | 6/2007 | Meyer et al. |
| 2007/0150014 A1 | 6/2007 | Kramer et al. |
| 2007/0150024 A1 | 6/2007 | Leyde et al. |
| 2007/0150025 A1 | 6/2007 | DiLorenzo et al. |
| 2007/0156179 A1 | 7/2007 | S.E. |
| 2007/0156450 A1 | 7/2007 | Roehm et al. |
| 2007/0156626 A1 | 7/2007 | Roehm et al. |
| 2007/0161919 A1 | 7/2007 | DiLorenzo |
| 2007/0162086 A1 | 7/2007 | DiLorenzo |
| 2007/0167991 A1 | 7/2007 | DiLorenzo |
| 2007/0173901 A1 | 7/2007 | Reeve |

| | | |
|---|---|---|
| 2007/0179534 A1 | 8/2007 | Firlik et al. |
| 2007/0179558 A1 | 8/2007 | Gliner et al. |
| 2007/0179584 A1 | 8/2007 | Gliner |
| 2007/0203548 A1 | 8/2007 | Pawelzik et al. |
| 2007/0208212 A1 | 9/2007 | DiLorenzo |
| 2007/0208390 A1 | 9/2007 | Von Arx et al. |
| 2007/0213785 A1 | 9/2007 | Osorio et al. |
| 2007/0233192 A1 | 10/2007 | Craig |
| 2007/0238939 A1 | 10/2007 | Giftakis et al. |
| 2007/0239210 A1 | 10/2007 | Libbus et al. |
| 2007/0239211 A1 | 10/2007 | Lorincz et al. |
| 2007/0239220 A1 | 10/2007 | Greenhut et al. |
| 2007/0244407 A1 | 10/2007 | Osorio |
| 2007/0249953 A1 | 10/2007 | Frei et al. |
| 2007/0249954 A1 | 10/2007 | Virag et al. |
| 2007/0250130 A1 | 10/2007 | Ball et al. |
| 2007/0250145 A1 | 10/2007 | Kraus et al. |
| 2007/0255147 A1 | 11/2007 | Drew et al. |
| 2007/0255155 A1 | 11/2007 | Drew et al. |
| 2007/0255330 A1 | 11/2007 | Lee et al. |
| 2007/0255337 A1 | 11/2007 | Lu |
| 2007/0260147 A1 | 11/2007 | Giftakis et al. |
| 2007/0260289 A1 | 11/2007 | Giftakis et al. |
| 2007/0265489 A1 | 11/2007 | Fowler et al. |
| 2007/0265508 A1 | 11/2007 | Sheikhzadeh-Nadjar et al. |
| 2007/0265536 A1 | 11/2007 | Giftakis et al. |
| 2007/0272260 A1 | 11/2007 | Nikitin et al. |
| 2007/0282177 A1 | 12/2007 | Pilz |
| 2007/0287931 A1 | 12/2007 | DiLorenzo |
| 2007/0288072 A1 | 12/2007 | Pascual-Leone et al. |
| 2007/0299349 A1 | 12/2007 | Alt et al. |
| 2007/0299473 A1 | 12/2007 | Matos |
| 2007/0299480 A1 | 12/2007 | Hill |
| 2008/0015651 A1 | 1/2008 | Ettori et al. |
| 2008/0015652 A1 | 1/2008 | Maile et al. |
| 2008/0021332 A1 | 1/2008 | Brainard, III |
| 2008/0021341 A1 | 1/2008 | Harris et al. |
| 2008/0021517 A1 | 1/2008 | Dietrich |
| 2008/0021520 A1 | 1/2008 | Dietrich |
| 2008/0027347 A1 | 1/2008 | Harris et al. |
| 2008/0027348 A1 | 1/2008 | Harris et al. |
| 2008/0027515 A1 | 1/2008 | Harris et al. |
| 2008/0033502 A1 | 2/2008 | Harris et al. |
| 2008/0033503 A1 | 2/2008 | Fowler et al. |
| 2008/0033508 A1 | 2/2008 | Frei et al. |
| 2008/0039895 A1 | 2/2008 | Fowler et al. |
| 2008/0046035 A1 | 2/2008 | Fowler et al. |
| 2008/0046037 A1 | 2/2008 | Haubrich et al. |
| 2008/0046038 A1 | 2/2008 | Hill et al. |
| 2008/0051852 A1 | 2/2008 | Dietrich et al. |
| 2008/0058884 A1 | 3/2008 | Matos |
| 2008/0064934 A1 | 3/2008 | Frei et al. |
| 2008/0071323 A1 | 3/2008 | Lowry et al. |
| 2008/0077028 A1 | 3/2008 | Schaldach et al. |
| 2008/0081962 A1 | 4/2008 | Miller et al. |
| 2008/0082132 A1 | 4/2008 | Annest et al. |
| 2008/0103548 A1 | 5/2008 | Fowler et al. |
| 2008/0114417 A1 | 5/2008 | Leyde |
| 2008/0119900 A1 | 5/2008 | DiLorenzo |
| 2008/0125820 A1 | 5/2008 | Stahmann et al. |
| 2008/0139870 A1 | 6/2008 | Gliner et al. |
| 2008/0146890 A1 | 6/2008 | LeBoeuf et al. |
| 2008/0146959 A1 | 6/2008 | Sheffield et al. |
| 2008/0161712 A1 | 7/2008 | Leyde |
| 2008/0161713 A1 | 7/2008 | Leyde et al. |
| 2008/0161879 A1 | 7/2008 | Firlik et al. |
| 2008/0161880 A1 | 7/2008 | Firlik et al. |
| 2008/0161881 A1 | 7/2008 | Firlik et al. |
| 2008/0161882 A1 | 7/2008 | Firlik et al. |
| 2008/0183096 A1 | 7/2008 | Snyder et al. |
| 2008/0183097 A1 | 7/2008 | Leyde et al. |
| 2008/0183245 A1 | 7/2008 | Van Oort et al. |
| 2008/0195175 A1 | 8/2008 | Balzer et al. |
| 2008/0200925 A1 | 8/2008 | Johnson |
| 2008/0208013 A1 | 8/2008 | Zhang et al. |
| 2008/0208074 A1 | 8/2008 | Snyder et al. |
| 2008/0208285 A1 | 8/2008 | Fowler et al. |
| 2008/0208291 A1 | 8/2008 | Leyde et al. |
| 2008/0208781 A1 | 8/2008 | Snyder |
| 2008/0215112 A1 | 9/2008 | Firlik et al. |
| 2008/0215114 A1 | 9/2008 | Stuerzinger et al. |
| 2008/0221644 A1 | 9/2008 | Vallapureddy et al. |
| 2008/0234598 A1 | 9/2008 | Snyder et al. |
| 2008/0249591 A1 | 10/2008 | Gaw et al. |
| 2008/0255582 A1 | 10/2008 | Harris |
| 2009/0018610 A1* | 1/2009 | Gharib et al. ............... 607/48 |
| 2009/0054795 A1 | 2/2009 | Misczynski et al. |
| 2009/0076567 A1 | 3/2009 | Fowler et al. |

FOREIGN PATENT DOCUMENTS

| | | |
|---|---|---|
| EP | 0402683 | 12/1990 |
| EP | 0713714 | 5/1996 |
| EP | 1139861 | 12/1999 |
| EP | 1070518 | 1/2001 |
| EP | 0944411 | 4/2001 |
| EP | 1145736 A2 | 10/2001 |
| EP | 1483020 | 12/2004 |
| EP | 1486232 | 12/2004 |
| EP | 1595497 | 11/2005 |
| EP | 1120130 | 12/2005 |
| EP | 1647300 | 4/2006 |
| EP | 1202775 | 9/2006 |
| GB | 2026870 | 2/1980 |
| GB | 2079610 | 1/1982 |
| WO | 9302744 | 2/1993 |
| WO | 9417771 | 8/1994 |
| WO | 0064336 A1 | 11/2000 |
| WO | 0108749 | 2/2001 |
| WO | 0064336 A9 | 6/2002 |
| WO | 03085546 | 10/2003 |
| WO | 2004036377 | 4/2004 |
| WO | 2004064918 | 8/2004 |
| WO | 2004069330 | 8/2004 |
| WO | 2004071575 | 8/2004 |
| WO | 2004075982 | 9/2004 |
| WO | 2004112894 | 12/2004 |
| WO | 2005007120 | 1/2005 |
| WO | 2005007232 | 1/2005 |
| WO | 2005028026 A1 | 3/2005 |
| WO | 2005053788 | 6/2005 |
| WO | 2005067599 | 7/2005 |
| WO | 2005101282 | 10/2005 |
| WO | 2006014760 | 2/2006 |
| WO | 2006019822 | 2/2006 |
| WO | 2006050144 | 5/2006 |
| WO | 2006122148 | 11/2006 |
| WO | 2007066343 A2 | 6/2007 |
| WO | 2007072425 | 6/2007 |
| WO | 2007124126 | 11/2007 |
| WO | 2007124190 | 11/2007 |
| WO | 2007124192 | 11/2007 |
| WO | 2007142523 | 12/2007 |

OTHER PUBLICATIONS

Bohning, D.E., et al.; "Feasability of Vagal Nerve Stimulation—Syncronized Blood Oxygenation Level-Dependent Functional MRI;" A Journal of Clinical and Laboratory Research: Investigative Radiology; vol. 36, No. 8 (Aug. 2001); pp. 470-479.

Boon, Paul, et al.; "Programmed and Magnet-Induced Vagus Nerve Stimulation for Refractory Epilepsy;" Journal of Clinical Neurophysiology vol. 18 No. 5; (2001); pp. 402-407.

Clark, K.B., et al.; "Posttraining Electrical Stimulation of Vagal Afferents with Concomitant Vagal Efferent Inactivation Enhances Memory Storage Process in the Rat;" Neurobiology of Learning and Memory, vol. 70, 364-373 (1998) Art. No. NL983863.

Clark, K.B., et al., "Enhanced Recognition Memory Following Vagas Nerve Stimulation in Human Subjects;" Nature Neuroscience, vol. 2, No. 1, (Jan. 1999) pp. 93-98.

Craig, A.D. (BUD); "Distribution of Trigeminothalamic and Spinothalamic Lamina I Terminations in the Macaque Monkey;" The Journal of Comparative Neurology, vol. 477, pp. 119-148 (2004).

DeGiorgio, Christopher M., et al.; "Vagas Nerve Stimulation: Analysis of Device Parameters in 154 Patients During the Long-Term XE5 Study;" Epilepsia, vol. 42, No. 8; pp. 1017-1020 (2001).

Devous, Michael D., et al.; "Effects of Vagas Nerve Stimulation on Regional Cerebral Blood Flow in Treatment-Resistant Depression;" National Institute of Mental Health—42nd Annual NCDEU Meeting: Poster Session II; Poster Abstracts, Jun. 10-13, 2002, 1 page; http://www.nimh.nih.gov/ncdeu/abstracts2002/ncdeu2019.cfm.

Hallowitz, R.A., et al.; "Effects Of Vagal Tolleys On Units Of Intralaminar and Juxtalaminar Thalamic Nuclei in Monkeys;" Brain Research, vol. 130 (1977), pp. 271-286.

Harry, J.D., et al.; "Balancing Act: Noise is the Key to Restoring the Body's Sense of Equilibrium;" IEEE Spectrum (Apr. 2005)pp. 37-41.

Henry, T.R., et al.; "Brain Blood-Flow Alterations Induced by Therapeutic Nerve Stimulation in Partial Epiepsy: I. Acute Effects at High and Low Levels of Stimulation;"Epilepsia vol. 39, No. 9; pp. 984-990 (1998).

Henry, MD, T.R.; "Therapeutic Mechanisms of Vagus Nerve Stimulation" Neurology, vol. 59 Suppl. 4 (Sep. 2002); pp. S3-S14.

King, M.D., "Effects of Short-Term Vagus Nerve Stimulation (VNS) on FOS Expression in Rat Brain Nuclei" 58th Annual Scientific Convention of the Society of Biological Psychiatry, (May 2003).

Klapper, M.D., et al., "VNS Therapy Shows Potential Benefit in Patients with Migraine and Chronic Daily Headache After 3 to 6 Months of Treatment (Preliminary Results)" 45th Annual Scientific Meeting of the American Headache Society (Jun. 2003).

Koo, B., "EEG Changes With Vagus Nerve Stimulation" Journal of Clinical Neurophysiology, vol. 18 No. 5 (Sep. 2001); pp. 434-441.

Labar, D., "Vagus Nerve Stimulation for 1 Year in 269 patients on Unchanged Antiepilectic Drugs" Seizure vol. 13, (2004) pp. 392-398.

Lockard et al., "Feasibility And Safety Of Vagal Stimulation In Monkey Model;" Epilepsia, vol. 31 (Supp. 2) (1990), pp. S20-S26.

Liebman, K.M. et al.; "Improvement in Cognitive Function After Vagal Nerve Stimulator Implantation;" Epilepsia, vol. 39, Suppl. 6 (1998) 1 page.

Malow, B.A., et al.; "Vagus Nerve Stimulation Reduces Daytime Sleepiness in Epilepsy Patients" Neurology 57 (2001) pp. 879-884.

McClintock, P., "Can Noise Actually Boost Brain Power" Physics World Jul. 2002; pp. 20-21.

Mori, T., et al.; "Noise-Induced Entrainment and Stochastic Resonance in Human Brain Waves" Physical Review Letters vol. 88, No. 21 (2002); pp. 218101-1-218101-4.

Rugg-Gunn, F.J., et al.; "Cardiac Arrhythmias in Focal Epilepsy: a Prospective Long-Term Study" www.thelancet.com vol. 364 (2004) pp. 2212-2219.

Rutecki, P.; "Anatomical, Physiological, and Theoretical Basis for the Antiepileptic Effect of Vagus Nerve Stimulation" Epilepsia, vol. 31 Suppl. 2; S1-S6 (1990).

Sahin, M.; et al.; "Improved Nerve Cuff Electrode Recordings with Subthreshold Anodic Currents," IEEE Transactions on Biomedical Engineering, vol. 45, No. 8 (Aug. 1998) pp. 1044-1050.

Schachter, S.C., et al.; "Progress in Epilepsy Research: Vagus Nerve Stimulation," Epilepsia, vol. 39, No. 7 (1998) pp. 677-686.

Tatum, W.O., et al.; "Ventricular Asystole During Vagus Nerve Stimulation for Epilepsy in Humans" American Academy of Neurologgy (1999) p. 1267 (See also pp. 1117, 1166, and 1265).

Tatum, W.O., et al.; "Vagus Nerve Stimulation and Drug Reduction" Neurology, vol. 56, No. 4 (Feb. 2001) pp. 561-563.

Terry et al., "The Implantable Neurocybernetic Prosthesis System", Pacing and Clinical Electrophysiology, vol. 14, No. 1 (Jan. 1991), pp. 86-93.

Tubbs, R.S., et al.; "Left-Sided Vagus Nerve Stimulation Decreases Intracranial Pressure Without Resultant Bradycardia in the Pig: A Potential Therapeutic Modality for Humans" Child's Nervous System Original Paper; Springer-Verlag 2004.

Valdez-Cruz, A., et al.; "Chronic Stimulation of the Cat Vagus Nerve Effect on Sleep and Behavior" Progress in Neuro-Psychopharmacology & Biological Psychiatry, vol. 26 (2002) pp. 113-118.

Vonck, K., et al. "The Mechanism of Action of Vagus Nerve Stimulation for Refractory Epilepsy—The Current Status", Journal of Neurophysiology, vol. 18 No. 5 (2001), pp. 394-401.

Ward, H., M.D., et al.; "Treatment-Refractory Obsessive-Compulsive Disorder: Potential Benefit of VNS Therapy" 23rd Annual Conference of the Anxiety Disorders Association of America (2007).

Woodbury, et al., "Vagal Stimulation Reduces the Severity Of Maximal Electroshock Seizures in Intact Rats. Use of a Cuff Electrode for Stimulating And Recording"; Pacing and Clinical Electrophysiology, vol. 14 (Jan. 1991), pp. 94-107.

Zabara, J. "Inhibition of Experimental Seizures in Canines by Repetivie Vagal Stimulation" Epilepsia vol. 33, No. 6 (1992); pp. 1005-1012.

Dodrill, Ph.D., et al.; "Effects of Vagal Nerve Stimulation on Cognition and Quality of Life in Epilepsy;" Epilepsy and Behavior, vol. 2 (2001); pp. 46-53.

Fromes, G. A.et al.; "Clinical Utility of On-Demand Magnet use with Vagus Nerve Stimulation;" AES Proceedings, p. 117.

George, M.S., et al.; "Open Trial of VNS Therapy in Severe Anxiety Disorders;" 156th American Psychiatric Association Annual Meeting; May 17-22, 2003.

George, M.S., et al.; "Vagus Nerve Stimulation; A New Tool for Brain Research and Therapy;" Society of Biological Psychiatry vol. 47 (2000) pp. 287-295.

Fanselow, E.E., at al.; "Reduction of Pentylenetetrazole-Induced Seizure Activity in Awake Rates by Seizure-Triggered Trigeminal Nerve Stimulation;" The Journal of Neuroscience, Nov. 1, 2000; vol. 20/21 ; pp. 8160-8168.

\* cited by examiner

THRESHOLD OPTIMIZATION FOR TISSUE STIMULATION THERAPY

BACKGROUND

1. Technical Field

The disclosed subject matter relates generally to the field of nerve stimulation. More specifically, the invention relates to a method and system of optimizing parameter settings for nerve stimulation.

2. Background Information

Various diseases and disorders of the nervous system are associated with abnormal neural discharge patterns. One treatment regimen for such diseases and disorders includes drug therapy. Another treatment technique includes the implantation of an implantable medical device having a pulse generator for electrically stimulating (i.e., applying an electrical signal to) a target location of the patient's neural tissue, such as a cranial nerve. In one such available treatment for epilepsy, the vagus nerve (the tenth cranial nerve) is electrically stimulated by a neurostimulator device substantially as described in one or more of U.S. Pat. Nos. 4,702,254, 4,867,164, and 5,025,807, all of which are incorporated herein by reference.

Some implantable pulse generators used for electrical stimulation of neurological tissue operate according to a therapy algorithm programmed into the device by a physician or other health care provider. One or more therapy parameters or the actual software running on the neurostimulator may be changed after implantation by reprogramming the neurostimulator via transcutaneous communication between an external programming device and the implanted neurostimulator. The ability to program (and later re-program) the implanted medical device ("IMD") permits a health care provider to customize the therapy provided by the IMD to the patient's needs, to update the therapy periodically should those needs change, and to update the software of the device, including the operating system, as improved and/or revised therapy regimens are developed.

However, in many cases, the physician will not know a suitable or optimal range of parameter settings within which to operate the neurostimulator. Each patient may have different levels of tolerance and reaction to nerve stimulation. Thus, some patients may have to be stimulated differently (e.g., different current levels, different frequencies, etc.) than other patients to respond to the therapy. Complicating selection of nerve stimulation therapies and parameters is the fact that many implantable medical devices are battery-operated. Different therapies may result in a different level of drain on the device's battery. All else being equal, one would prefer for the battery to last as long as possible.

BRIEF SUMMARY

Methods and systems for determining an optimal therapeutic window of parameter settings for nerve stimulation therapy are described herein. The disclosed techniques generally utilize one or more parameter sweeps to determine upper and lower threshold settings for an individual patient. The determination of the optimal therapeutic window may be performed during surgery to implant an implantable medical device. In one embodiment, this could be accomplished using a temporary electrode coupled to the nerve during the surgical procedure. The temporary electrode may be removed at the conclusion of the optimization process. Alternatively, a permanent electrode for sensing electrical activity on the nerve may be attached to the nerve and coupled to the implantable medical device for non-invasively optimizing therapeutic windows after surgery.

In at least one embodiment, a method comprises delivering an electrical signal to a nerve according to at least a first and second parameter. The method also comprises measuring an electrical response of the nerve to the electrical signal. In addition, the method comprises adjusting the first parameter while the second parameter remains constant. The method further comprises repeating the aforementioned acts to acquire a plurality of electrical responses and determining a lower threshold setting and an upper threshold setting from the plurality of electrical responses.

In another embodiment, a method comprises delivering a plurality of electrical signals to a nerve according to a plurality of current amplitudes and a constant pulse width. The method additionally comprises recording a plurality of electrical responses of the nerve to the plurality of electrical signals. Furthermore, the method comprises determining at least one lower threshold setting and at least one upper threshold setting from the plurality of electrical responses of the nerve.

In a further embodiment, a system comprises a processor and software executable on the processor. The software causes the processor to instruct an implantable medical device to deliver a plurality of electrical signals to a nerve according to at least first and second parameters. The first parameter is iteratively adjusted while the second parameter remains fixed. The software also instructs the processor to detect a plurality of electrical responses of the nerve to the plurality of electrical signals applied to the nerve, and to determine a lower threshold setting and an upper threshold setting from the plurality of electrical responses based on a fixed second parameter.

The described methods and systems provide a user with settings at which an implantable medical device can operate with improved (e.g., optimal) energy efficiency. As a result, a physician is provided with a known, and generally optimal, range of parameter settings for therapy for an individual patient without the need for extensive trial and error.

The foregoing has outlined rather broadly certain features and advantages of the disclosed embodiments in order that the detailed description that follows may be better understood. Additional features may be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

NOTATION AND NOMENCLATURE

Figure 1:
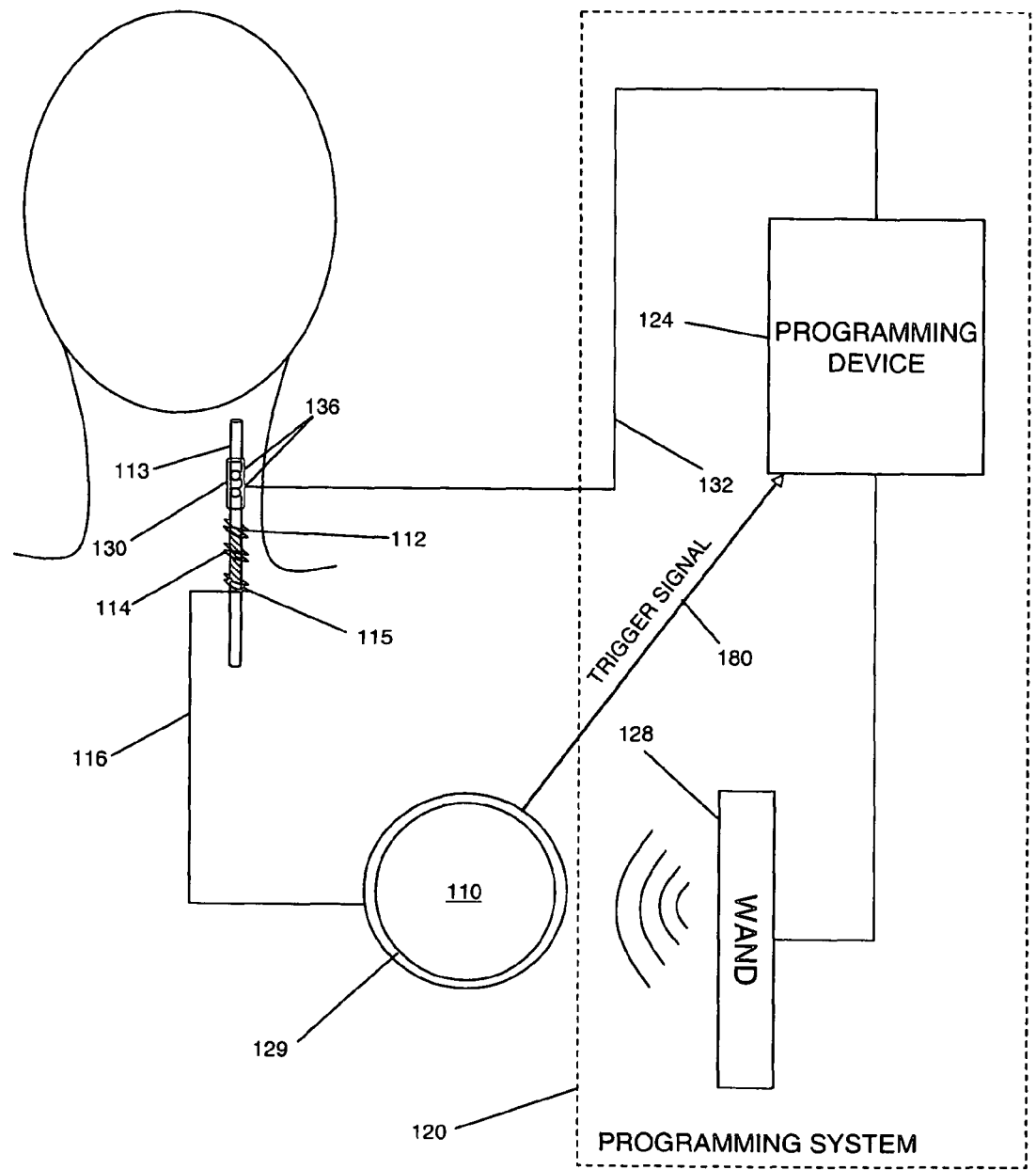
FIG. 1 depicts, in schematic form, an implantable medical device, in accordance with a preferred embodiment of the invention, implanted within a patient and programmable by an external programming system.

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "couple" or "couples" is intended to mean either an indirect or direct electrical connection. Thus, if a first device couples to a second device, that connection may be through a direct electrical connection, or through an indirect electrical connection via other devices and connections.

"Compound action potential" means a group of almost synchronous nerve fiber action potentials from the trunk of a motor, sensory, or mixed nerve. Compound action potentials may be evoked by nerve stimulation and are recorded as a multi-peaked summed action potential.

"Parameter sweep" means a test conducted employing at least two parameters that can be varied, the test progressively increasing or decreasing a first parameter within a specified range while keeping a second parameter constant.

DETAILED DESCRIPTION OF THE PREFERRED EMBODIMENTS

The present invention is susceptible to implementation in various embodiments. The disclosure of specific embodiments, including preferred embodiments, is not intended to limit the scope of the invention as claimed unless expressly specified in the claims. In addition, persons skilled in the art will understand that the invention has broad application. Accordingly, the discussion of particular embodiments is meant only to be exemplary, and does not imply that the scope of the disclosure, including the claims, is limited to specifically disclosed embodiments.

The following description is presented largely in terms of vagus nerve stimulation ("VNS"), in which the electrical signal is applied to the vagus nerve. However, the disclosure and claims that follow are not limited to VNS, and may be applied to the delivery of an electrical signal to modulate the electrical activity of other cranial nerves such as the trigeminal and/or glossopharyngeal nerves, or to other neural tissue such as one or more brain structures of the patient, spinal nerves, and other spinal structures. Further still, other embodiments of the invention can be implemented to stimulate tissue other than nerves or neural tissue, such as cardiac tissue.

It is recognized that a minimum level of stimulation by a battery-powered VNS device is required to evoke action potentials on a nerve. The minimum stimulation level may be a function of a number of different parameters and is generally unique to each patient. Further, as the level of stimulation is increased from the minimum level, the ability to invoke action potentials may also increase. There is, however, a point of "diminishing returns" in that, at some point, further increases to the level of stimulation does not produce a statistically significant increase in action potential response, and thus only serves to unnecessarily drain the battery that powers the VNS device.

The following embodiments assist in the determination, for a given patient, of a minimum level as well as a maximum level that generally corresponds to a point of diminishing returns. Measurements are made on the patient to facilitate these computations. In at least some embodiments, the measurements are made during surgery to implant the VNS device. The process comprises implanting the VNS device and employing a temporary cuff electrode assembly that is coupled to the target nerve. The cuff electrode assembly connects to an external system that initiates the process of stimulating the nerve and measuring the response. After the measurements are made, the cuff electrode assembly is removed from the patient and the implantation surgery can be completed.

FIG. 1 illustrates an implantable medical device ("IMD") 110 implanted in a patient. The IMD 110 may be representative of any of a variety of medical devices. At least one preferred embodiment of the IMD 110 comprises a neurostimulator for applying an electrical signal to a neural structure in a patient, particularly a cranial nerve such as a vagus nerve 113. As used herein "stimulate" and "modulate" both refer to the delivery of such an electrical signal to a target body structure, regardless of whether the signal causes a particular effect such as an induction of an action potential in a stimulated nerve.

Referring still to FIG. 1, a lead assembly comprising one or more leads 116 is coupled to the IMD 110 and includes one or more electrodes, such as electrodes 112 and 114. Each lead 116 has a proximal end that connects to the IMD 110 and a distal end on which one or more electrodes are provided. The outer housing (or "can") 129 of the IMD 110 preferably is electrically conductive and thus may also function as an electrode. The electrodes, such as electrodes 112, 114 and can 129, can be used to stimulate and/or sense the electrical activity of the associated tissue (e.g., the vagus nerve 113). Strain relief tether 115 comprises an attachment mechanism that attaches the lead assembly 116 to the nerve 113 to provide strain relief. An example of a suitable strain relief tether is described in U.S. Pat. No. 4,979,511, incorporated herein by reference.

In the embodiment of FIG. 1, a removable cuff assembly 130 is applied to the nerve 113, such as during surgery to implant the IMD 110, and coupled to an external programming system 120 to determine optimal parameter settings for the patient receiving the IMD 110. The removable cuff assembly 130 includes one or more electrodes 136. The removable cuff assembly 130 is easily attached to, and removed from, the nerve 113 during implantation and with minimal risk of damaging the nerve. In accordance with various preferred embodiments, the removable cuff assembly insulates the electrodes 136 from body tissues (other than nerve 113). Lead assembly 132 is coupled to a programming system 120. The electrodes 136 in the cuff assembly 130 are used to detect electrical activity, such as voltage or compound action potential response on the nerve 113 as a result of an electrical signal generated by the IMD 110 and applied to the nerve.

Referring still to FIG. 1, the programming system 120 comprises a programming device 124 coupled to a wand 128. The programming device 124 may comprise a personal computer, handheld computer, or other suitable computing devices consistent with the description contained herein. As explained below, the IMD 110 includes a transceiver (such as a coil) and the wand 128 also includes a transceiver. The transceivers in the IMD 110 and wand 128 permit signals to be communicated wirelessly and non-invasively between them. Via the wand 128, the programming system 120 provides one or more parameters to the IMD for the IMD to generate a programmed electrical signal. The programming system also commands the IMD 110 to apply electrical signal to the nerve in accordance with the programming system-specified parameter(s). Electrical activity on the nerve as a result of the IMD-provided electrical signal is sensed by the cuff assembly 130, and communicated to the programming system 120. Following implantation, the programming system 120 can be used to monitor the performance of the implanted IMD 110 and download new programming information into the device to alter its operation as desired.

Figure 2:
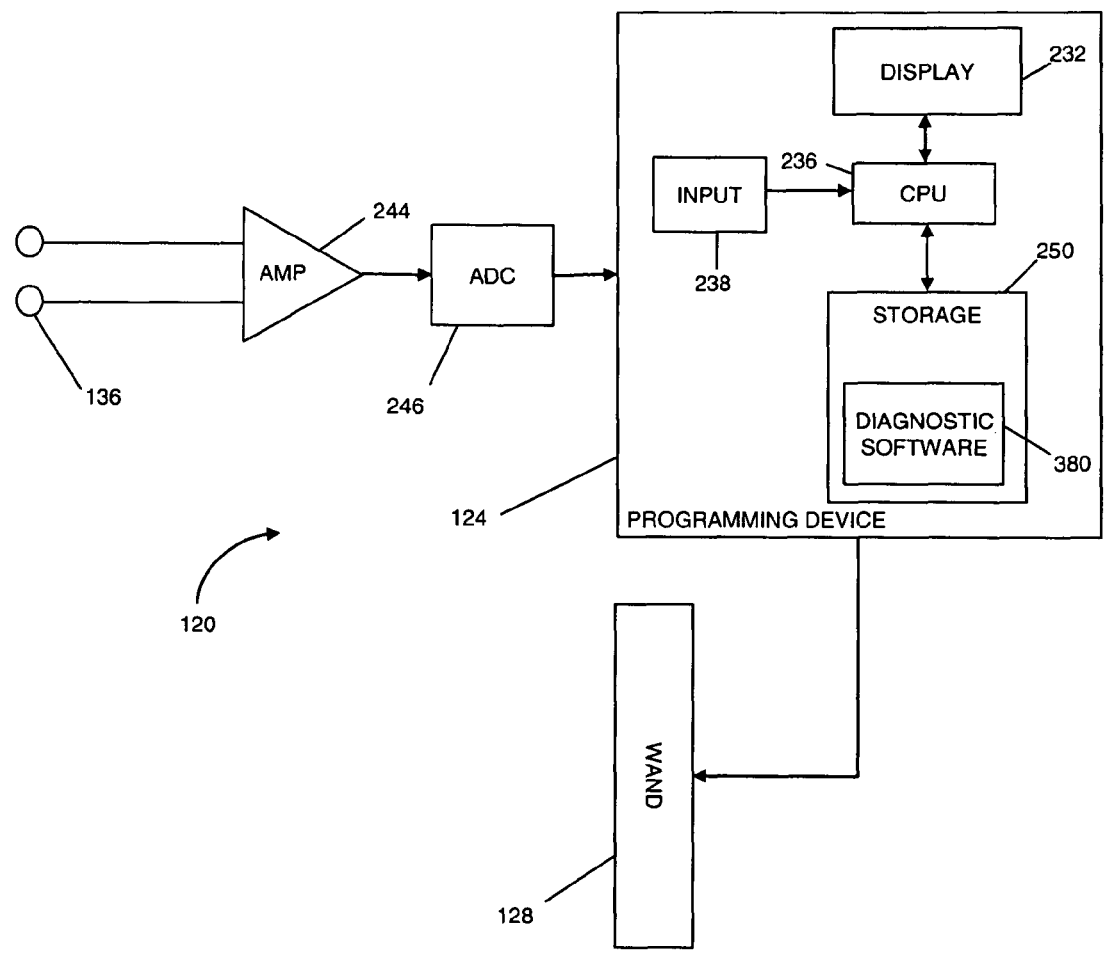
FIG. 2 is a block diagram of an embodiment of the programming system of FIG. 1.

FIG. 2 shows a block diagram of one embodiment of the programming system 120. As shown, the programming system 120 includes the programming device 124, the wand 128, an amplifier 244, and an analog-to-digital (A/D) converter 246. The programming device 124 preferably comprises a handheld computer. The programming system 120 generally assists, controls, and/or programs the IMD 110 and receives signals representative of the electrical activity on the target nerve 113 via electrodes 136. Under the control of the programming system 120, the IMD 110 generates an electrical pulse signal to stimulate nerve 113 in a patient.

Programming device 124 preferably includes a central processing unit (CPU) 236 such as a low-power, mixed-signal microcontroller. In general, any suitable processor can be used to implement the functionality performed by the programming device 124 as explained herein. It will be appreciated that some features of the programming system 120 may also be provided in whole, or in part, by the IMD 110, and vice versa. Thus, while certain features of the present invention may be described as being included as part of the IMD 110, it is not intended thereby to preclude embodiments in which the features are provided by the programming system 120. Likewise, describing certain features herein as part of the programming system 120 is not intended to preclude embodiments in which the features are included as part of the IMD 110.

The CPU 236 is preferably coupled to storage 250. The CPU 236 may interpret, manipulate, and/or analyze the data received from removable cuff assembly electrodes 136. The storage 250 may comprise volatile (e.g., random access memory) and/or non-volatile storage (e.g., read only memory (ROM), electrically-erasable programmable ROM (EEPROM), Flash memory, etc.). Storage 250 may comprise any suitable storage medium. Examples of suitable storage media include without limitation, USB flash drives, Compact Flash cards, memory sticks, Smart Media cards, Secure Digital (SD) cards, xD cards, CD-ROM, DVD-ROM, tape drives, Zip disks, floppy disk, RAM, hard drives, etc. The storage 250 may be used to store code (e.g., diagnostic software 380, discussed below) that is executed by the CPU 236. The executable code may be executed directly from the non-volatile memory or copied to the volatile memory for execution therefrom.

The storage 250 may also be used to store the parameter settings, any one or more of which can be programmed into the IMD 110 by the programming system 120. The parameters include, for example, pulse width, current amplitude, frequency, on time, off time, etc. The parameters define the nature of the electrical signal to be delivered to the nerve 113.

In accordance with certain embodiments, the programming device 124 includes the diagnostic program 380. During implantation, the programming system 120 can be used and the diagnostic software 380 executed to cause the IMD 110 to repeatedly stimulate the patient's nerve 113 in accordance with various programming system-provided parameters. Through cuff assembly 130, the programming system is informed of the electrical activity on the nerve that results from the various IMD-generated electrical signals. The resulting evoked electrical activity and sensed data are analyzed by, for example, the programming system 120 to determine lower and upper threshold settings. In at least one embodiment, the diagnostic software 280 causes a first stimulation parameter (e.g., current amplitude) to be iteratively adjusted while keeping a second parameter (e.g., pulse width) constant. This process is referred to as a parameter sweep. A lower threshold setting represents the parameter settings that correspond to a lower threshold. The term "lower threshold" is the minimum electrical stimulation level necessary to evoke a compound action potential response.

An upper threshold setting represents the parameter settings corresponding to an upper threshold. The upper threshold is an electrical stimulation level above which no statistically significant increase in action potential is obtainable by further increasing the level of stimulation (i.e., the point of diminishing returns).

As explained above, the diagnostic software 380 operates to adjust iteratively a first parameter (e.g., current amplitude) while holding a second parameter constant (e.g., pulse width). Once that parameter sweep is completed, the diagnostic software 380 may adjust the second parameter (e.g., pulse width) to one or more different settings and again perform a first parameter sweep for each subsequent second parameter setting. The diagnostic software 380 is described in more detail below.

The programming device also includes a display 232. Preferably, the programming device 124 is capable of displaying a waveform of a compound action potential from a nerve on the display 232. In preferred embodiments, a user may input parameter settings using an input device 238 through a graphical user interface on the display 232, or other input means. Storage 250 stores the measured compound action potential amplitudes received from sensing electrode 130 as well as the corresponding parameter settings which caused the compound action potential.

In certain embodiments, the programming system 120 comprises an amplifier 244 and an A/D converter 246. The amplifier 244 and A/D converter 246 may be part of the programming device 124 or separate from the programming device 124. The amplifier 244 amplifies analog signals received from sensing electrodes 136 while the A/D converter 246 converts the amplified analog signal from the electrodes 136 to a digital signal representation for the programming device 124 to process. In this embodiment, the parameter settings, lower threshold settings, upper threshold settings, and measured amplitudes are stored on storage 250.

Figure 3:
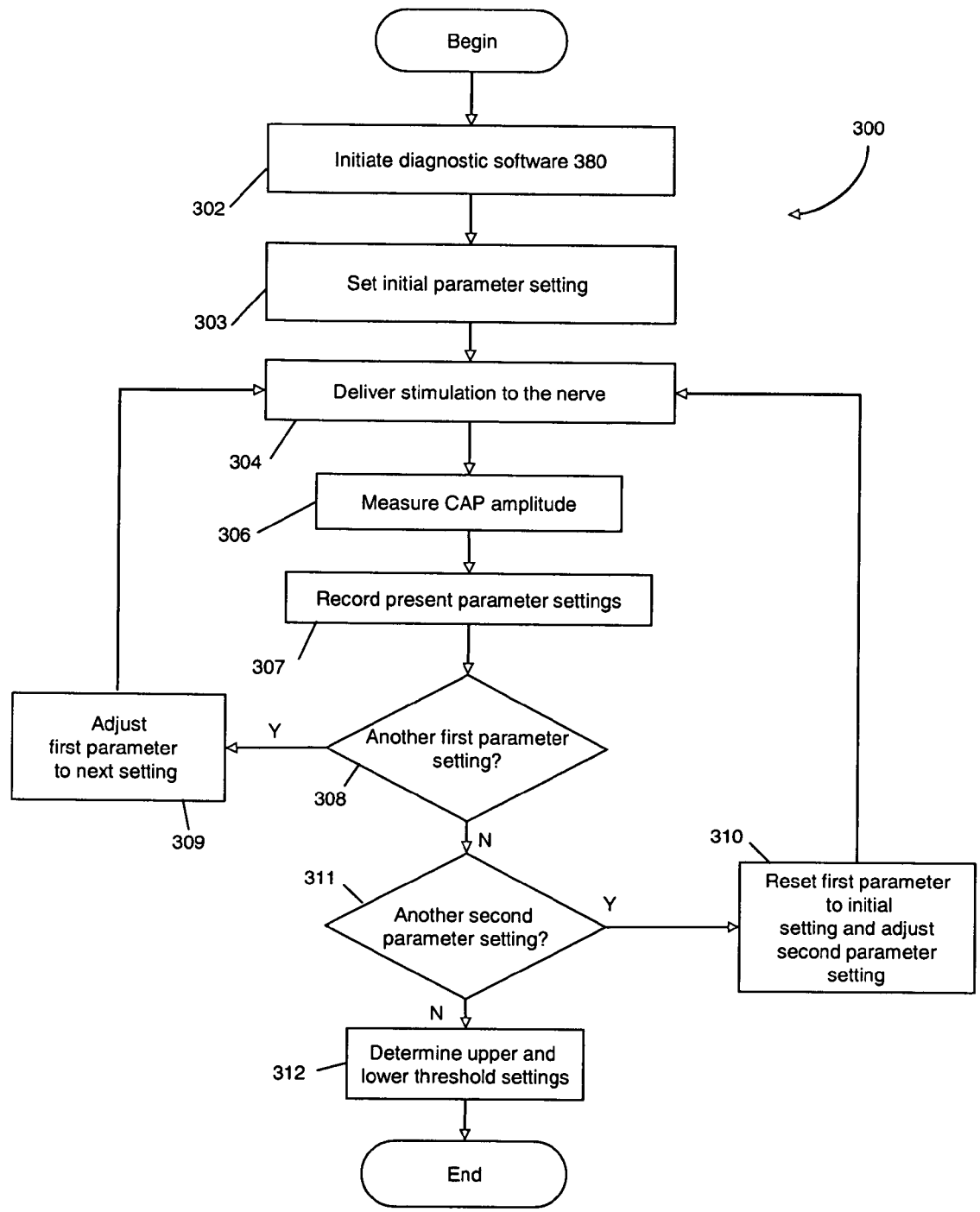
FIG. 3 illustrates a flow diagram of an embodiment of a method for threshold optimization for nerve stimulation therapy.

FIG. 3 illustrates a flow chart depicting an embodiment of a method 300 for threshold optimization for nerve stimulation therapy. In this embodiment, the method 300 is performed intra-operatively i.e. during implantation of the IMD 100. Alternatively, with implantation of a permanent sensing electrode, method 300 may be performed after implantation of the IMD 110. Preferably, the method 300 is performed automatically (i.e., without the need for any user intervention) via diagnostic software 380. However, in some embodiments, the entire method or portions of the method are performed manually where certain actions require user input.

In block 302, the diagnostic software 380 is initiated. Typically, a user initiates the diagnostic software 380 by way of the programming device 124. The programming device 124 then instructs the IMD 110 to proceed and execute the diagnostic software 380. The diagnostic software 380 preferably is stored in storage 250 of programming device 124 and is executed by the CPU 236. Alternatively, the diagnostic software 380 is downloaded from the programming device 124 to the IMD 110 immediately before starting method 300. In another embodiment, the diagnostic software 380 is preloaded in the IMD 110. In yet other embodiments, method 300 is performed manually without the need for diagnostic software 380.

In general, the diagnostic software 380 contains one or more parameters at pre-programmed settings at which to stimulate the nerve to determine lower and upper threshold settings. The diagnostic software 380 may also define a preset range for each parameter. By way of example only, the diagnostic software may contain instructions to stimulate the nerve at three pulse widths in 100 μs increments (250 μsec, 350 μsec, and 450 μsec,) and at each pulse width, testing seven current levels ranging from 0.25 mA to 1.75 mA at 0.25 mA intervals (See Table 1).

TABLE 1

| Pulse width 250 μsec Output Current (mA) | Pulse width 350 μsec Output Current (mA) | Pulse width 450 μsec Output Current (mA) |
| --- | --- | --- |
| 0.25 | 0.25 | 0.25 |
| 0.5 | 0.5 | 0.5 |
| 0.75 | 0.75 | 0.75 |
| 1.0 | 1.0 | 1.0 |
| 1.25 | 1.25 | 1.25 |
| 1.5 | 1.5 | 1.5 |
| 1.75 | 1.75 | 1.75 |

However, the diagnostic software 380 may comprise any number of settings for a particular parameter. In an actual implementation, a "sweep" could consist of any desired step change in current and pulse width, e.g., smaller or larger increments than the 0.25 mA and 100 μsec examples discussed above. By providing smaller step sizes, a better resolution of the threshold window may be provided. In alternative embodiments, before implantation, a user may enter the desired range, parameters, parameter settings, and/or parameter increments to be tested into the programming device 124.

The diagnostic software 380 also comprises an initial parameter setting which is incapable of evoking a compound action potential response in a nerve. In block 303, the programming device 124 instructs the IMD 110 to begin at the initial parameter setting by programming the IMD 110 with the initial parameter values. Once the IMD 110 has been set to the initial parameter values, the IMD 110 delivers the electrical signal to the nerve in block 304 according to the initial parameter setting in block 303. Typically, the programming device 124 instructs the IMD 110 to deliver the electrical signal, which preferably comprises one more pulses in accordance with the specified parameter settings (e.g., 10 pulses/sec at a specified current amplitude for 5 seconds).

In block 306, programming device 124 measures and stores the amplitudes of the response in data storage 250. In embodiments where a plurality of electrical pulses are delivered at a parameter setting, programming device 124 calculates, for example, an average amplitude from the plurality of responses caused by the plurality of electrical pulses. The programming device 124 then records the calculated average amplitude in storage 250. Further, in block 307, the present parameter setting programmed into the IMD 110 is recorded in data storage 250 and associated with stored response data.

In further embodiments, block 306 comprises detecting a trigger signal 180 from the IMD 110 (FIG. 1). The trigger signal 180 is asserted by the IMD 110 upon the IMD providing an electrical signal to the nerve 113. The trigger signal 180 thus indicates when the nerve is being stimulated by the IMD 110. The programming device 124 may ignore electrical activity sensed from the nerve until it receives a trigger signal 180 from the IMD 110 and then begin sensing the nerve's electrical activity for a period of time based on the assertion of the trigger signal. The trigger signal enables the programming device 124 to avoid recording shock artifacts and activity unrelated to the actual nerve response.

In block 308, the diagnostic software 380 checks to see if further first parameter settings (e.g., current amplitudes) are to be tested. If additional first parameter settings to be tested during the present parameter sweep, the method proceeds to block 309. At block 309, programming device 124 instructs the IMD 110 to adjust iteratively the first parameter (e.g., current) while keeping the second parameter (e.g., pulse width) constant. In other words, electrical signals are delivered at a plurality of different current amplitudes, but at a constant pulse width. Examples of parameters that may be varied include without limitation current amplitude, pulse-width, frequency, duty cycle, etc. Any combination and number of parameters may be tested. After adjusting the first parameter, the programming device 124 then instructs the IMD 110 to deliver the electrical signal at the new parameter setting at block 304.

If all first parameter settings have been tested for a given second parameter setting, the method 300 proceeds to block 311. If the diagnostic software 380 contains instructions for additional second parameters to be tested, the method proceeds to block 310. At block 310, the second parameter is adjusted. For example, the pulse width may be changed from 250 μsec to 350 μsec. The programming device 124 also instructs the IMD 110 to reset the first parameter to its initial setting. The process then proceeds to block 304 and the first parameter sweep is repeated, this time with a different second parameter.

Once the diagnostic software 380 has completed parameter sweeps for all of the second parameter settings, the method 300 proceeds to block 312. In block 312, the programming system 120 determines the lower and upper threshold settings for each second parameter setting. Thus, for example, if a current amplitude sweep is performed for each of three pulse widths, the programming system 120 determines three sets of lower/upper threshold settings—one for each pulse width. The lower threshold setting comprises the lowest first parameter setting (e.g., current amplitude) at which a compound action potential is detected via the electrodes 136 for a given second parameter setting. In an alternative embodiment (not shown), upper and/or lower thresholds may be determined at any desired point within a sweep of the first parameter or the second parameter. Such a method could be used to abort unnecessary parameter sweep settings and thereby avoid unnecessary electrical signals being delivered to the patient. For example, once an upper threshold has been determined during a first parameter sweep, the system may abort any programmed first parameter settings exceeding that for the determined upper threshold.

The upper threshold setting comprises a maximum first parameter setting above which, all else being equal, no statistically significant increase in action potential magnitude is observed for a given second parameter setting. In one embodiment, a current amplitude parameter sweep is performed for a given pulse width. The current amplitudes programmed into the IMD 110 start low and are increased by the programming system 120. For each IMD current amplitude, the programming system senses the resulting electrical response (voltage potential) induced on the nerve. At some point, the increase in nerve response voltage potential resulting from one current amplitude to the next (i.e. higher) current amplitude, while possibly increasing, ceases to increase very much. A determination can thus be made that, if the nerve response voltage potential does not increase more than a specified amount, the upper threshold setting has been reached. The specified amount can be expressed in terms of voltage potential or a percentage of a predetermined value of voltage potential. The specified amount can be hard-coded into the diagnostic software 380 or programmable.

Figure 4:
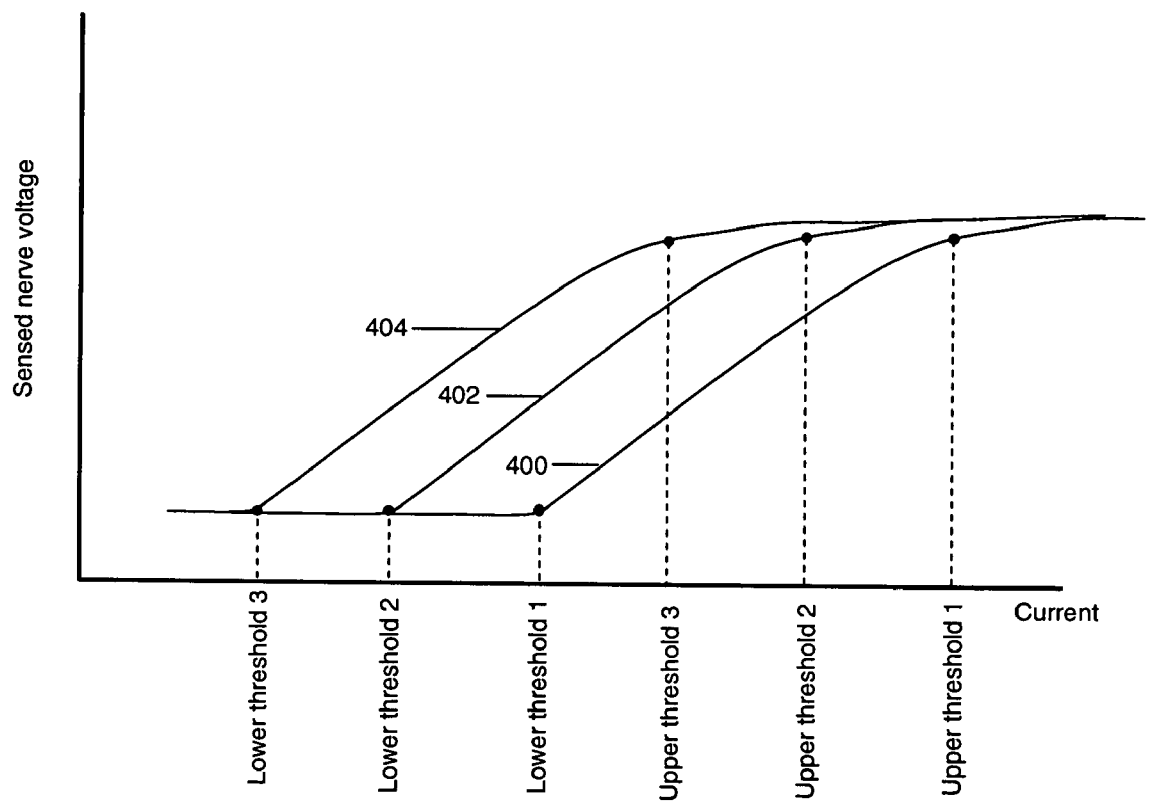
FIG. 4 illustrates a sample plot as a result of the disclosed method. Each curve represents a graph of sensed nerve responses (voltage) at different current (or other parameter) settings and at a constant pulse width.

Once the upper threshold and lower threshold settings have been determined, the parameter settings are stored in storage 250 and identified as the upper and lower threshold settings. In a preferred embodiment, the result of method 300 is, at least in part, the lower and upper threshold settings corresponding to each second parameter setting (pulse width). The result of method 300 may also include a set of parameter settings between the lower and upper threshold settings as well as the corresponding recorded compound action potential amplitudes. The upper and lower threshold settings may be downloadable or recorded on removable storage medium. A physician or user may utilize the information to plot customized operating curves for each patient on the display 232. An example of such a plot is shown in FIG. 4. FIG. 4 shows three curves 400, 402, and 404 with each curve plotting sensed nerve voltage versus signal current amplitude. The three curves 400, 402, and 404 illustrate progressively increasing pulse width settings from right to left, respectively. For each curve, the lower and upper threshold settings are illustrated.

In a variation of method 300, amplitudes and parameters may not be recorded until a lower threshold is reached. If a compound action potential response has not occurred in response to electrical stimulation, the method 300 may proceed to a separate lower threshold determining step (not shown). If a lower threshold has not been reached, blocks 304, 306 and 308 are repeated until the programming device 120 determines that a compound action potential response occurs. Once a lower threshold is reached, the data i.e. parameter setting, compound action potential amplitude, is recorded in data storage 250 and identified as a lower threshold setting. After a lower threshold has been reached, data may be continuously recorded in storage 250 until an upper threshold is reached.

In an embodiment, the programming device performs a separate upper threshold determining step after block 307 (not shown). If the programming device 124 has determined that an upper threshold has not been reached, then the method 300 may proceed to 308. However, if the programming device has determined that an upper threshold has been reached, the corresponding parameter settings may be identified and the method 300 may proceed to block 311.

The system and method described herein cause measurements to be made for a given patient to determine, for each of a plurality of pulse widths (or other parameter), the minimum amount of current (or other parameter) needed to evoke an electrical response on a nerve and an upper amount of current above which it is determined that no further therapeutic benefit is achieved and battery would simply be wasted. Healthcare providers can use this data to treat the patient. The data includes a suitable or optimal range of values to be programmed for that particular patient.

Although certain embodiments of the present invention have been described in detail, it should be understood that various changes, substitutions and alterations may be made herein without departing from the spirit and scope of the invention as defined by the appended claims.

What is claimed is:

1. A method, comprising:
  a) automatically delivering an electrical signal to a cranial nerve of a patient according to at least a first parameter and a second parameter;
  b) automatically measuring an electrical response of the nerve to the electrical signal;
  c) automatically adjusting the first parameter while keeping the second parameter at a first test setting;
  d) automatically repeating operations a) through c) to acquire a first plurality of electrical responses;
  e) determining a lower threshold for the first parameter with the second parameter at the first test setting and an upper threshold for the first parameter with the second parameter at the first test setting, based on the first plurality of electrical responses, wherein the upper threshold corresponds to an electrical signal level above which increasing the first parameter does not cause a significant increase in the electrical response;
  automatically adjusting the second parameter to at least one different test setting and then automatically repeating operations (a) through (e) to determine lower and upper thresholds for the first parameter with the second parameter at the different test setting;
  recording the determined lower and upper thresholds and the corresponding test settings for the first and second parameters;
  determining customized treatment parameters for the patient, based on the recorded information; and
  programming an implantable medical device (IMD) for the patient to treat the patient according to the customized treatment parameters.

2. The method of claim 1, wherein the lower threshold corresponds to a minimum electrical signal level necessary to evoke a compound action potential response on the nerve.

3. The method of claim 1, further comprising, prior to operation (a), defining an initial first and second parameter setting, wherein said initial first and second parameter setting defines an electrical signal that does not evoke a compound action potential response.

4. The method of claim 1, wherein said first parameter comprises a parameter selected from the group consisting of current amplitude, frequency, pulse width, on time, off time, and duty cycle.

5. The method of claim 1, further comprising:
  implanting the IMD into the patient; and
  wherein operations (a) through (d) are performed during implantation of the IMD into of the patient.

6. The method of claim 1, wherein (b) further comprises measuring an electrical response of said nerve to a trigger signal received from an electrical signal generator, said trigger signal indicating an occurrence of said electrical signal.

7. The method of claim 1, wherein operations (a) through (e) are performed after implantation of the IMD into the patient.

8. The method of claim 1, further comprising attaching a temporary electrode to said nerve to measure said electrical response.

9. A method according to claim 1, wherein:
  the first parameter pertains to current amplitude and the second parameter pertains to pulse width.

10. The method of claim 9, further comprising defining a range of current amplitudes for the first parameter prior to operation (a).

11. The method of claim 9, wherein the operation of recording the determined lower and upper threshold and the corresponding test settings for the first and second parameters comprises storing measurements of the electrical responses and the corresponding current amplitudes and pulse widths on a tangible storage medium.

12. The method of claim 9, wherein the operation of determining a lower threshold comprises determining a current amplitude and a pulse width that corresponds to a minimum electrical signal level necessary to evoke a compound action potential.

13. The method of claim 9, wherein determining an upper threshold comprises determining a current amplitude and a pulse width corresponding to an electrical signal level where increasing the current amplitude does not cause a significant increase in the electrical response.

14. A method according to claim 1, further comprising:
using the recoded information to plot multiple operating curves, wherein each operating curve depicts measured behavior of the cranial nerve of the patient at a different setting for the second parameter.

15. A system, comprising:
a processor;
an amplifier and an analog-to-digital (A/D) converter coupled to the processor, the amplifier and A/D converter operable to convert data from a sensor electrode coupled to a cranial nerve of a patient into data for the processor;
a transceiver coupled to the processor, the transceiver operable to communicate with an implantable medical device (IMD);
a storage medium responsive to the processor; and
software stored in the storage medium and executable on the processor, wherein the software, when executed, causes the processor to perform operations comprising:
  a) instructing the IMD to deliver a plurality of electrical signals to the cranial nerve according to at least first and second parameters, wherein the first parameter is iteratively adjusted automatically, while the second parameter remains fixed at a first test setting;
  b) automatically detecting a first plurality of electrical responses of the nerve to the plurality of electrical signals;
  c) automatically determining a lower threshold for the first parameter with the second parameter at the first test setting and an upper threshold for the first parameter with the second parameter at the first test setting, based on the first plurality of electrical responses, wherein the upper threshold corresponds to an electrical signal level above which increasing the first parameter does not cause a significant increase in the electrical response;
automatically executing one or more iterations of a process comprising:
  i) adjusting the second parameter to a different test setting and then
  ii) repeating operations (a) through (c) to determine a lower threshold and an upper threshold for the first parameter with the second parameter at the different test setting; and
automatically recording multiple sets of lower and upper thresholds and the corresponding test settings for the first and second parameters, with each set corresponding to a different setting for the second parameter;
determining customized treatment parameters for the patient, based on the recorded information; and
programming an implantable medical device (IMD) for the patient to treat the patient according to the customized treatment parameters.

16. The system of claim 15, wherein the system comprises a programming device coupled to a removable cuff assembly comprising at least one sensing electrode.

17. The system of claim 15, wherein the operations further comprise:
detecting a trigger signal received by the system directly from said IMD; and
automatically detecting the first plurality of electrical responses of the nerve to the plurality of electrical signals, in response to detecting the trigger signal.

18. A system according to claim 15, wherein the operations further comprise:
using the recoded information to plot multiple operating curves, wherein each operating curve depicts measured behavior of the cranial nerve of the patient at a different setting for the second parameter.

* * * * *